United States Patent [19]

Tomkins et al.

[11] Patent Number: 4,668,507

[45] Date of Patent: May 26, 1987

[54] CORROSION RESISTANT INSECTICIAL COMPOSITION

[75] Inventors: David A. Tomkins; William S. Tait, both of Racine; Donald J. Duda, Kenosha, all of Wis.

[73] Assignee: S. C. Johnson & Son, Inc., Racine, Wis.

[21] Appl. No.: 796,354

[22] Filed: Nov. 7, 1985

Related U.S. Application Data

[63] Continuation of Ser. No. 596,769, Apr. 4, 1984, abandoned.

[51] Int. Cl.$^4$ ............................ A61L 9/04; C23F 11/00
[52] U.S. Cl. ...................................... 424/45; 252/389.2
[58] Field of Search ........................ 424/45; 252/389.2

[56] References Cited

U.S. PATENT DOCUMENTS

| 3,958,007 | 5/1976 | Wommack, Jr. | 514/482 |
| 4,201,764 | 5/1980 | French et al. | 424/45 |
| 4,219,433 | 8/1980 | Manabe et al. | 252/389.2 |
| 4,338,209 | 7/1982 | Manabe et al. | 252/389.2 |
| 4,347,154 | 8/1982 | Simmons | 424/45 |
| 4,457,934 | 7/1984 | Wong | 514/277 |

FOREIGN PATENT DOCUMENTS 0006212  1/1980  European Pat. Off. ............. 424/45

*Primary Examiner*—Albert T. Meyers
*Assistant Examiner*—F. Krosnick

[57] ABSTRACT

A corrosion resistant insecticidal composition for use in aerosol containers includes an organophosphorous pesticide, an emulsifier, an aerosol propellant, an aqueous carrier and as a corrosion inhibiting system, an organic corrosion inhibitor and an inorganic corrosion inhibitor.

2 Claims, No Drawings

CORROSION RESISTANT INSECTICIDAL COMPOSITION

This is a continuation of co-pending application Ser. No. 596,769 filed on Apr. 4, 1984, now abandoned.

BACKGROUND OF THE INVENTION

The invention relates to a corrosion resistant insecticidal composition for use in aerosol cans. In particular, it relates to an aqueous emulsified organic phosphorous pesticide composition which retards corrosion, especially pitting corrosion, in tin-plated steel aerosol cans.

Pressurized, water-based emulsified organophosphorous pesticides are known to be highly corrosive to tin-plated steel aerosol cans. In general, such aerosol cans are subject to at least three types of corrosion; general corrosion cathodic delamination of the can liner and pitting corrosion. The theory and mechanism of general corrosion and pitting corrosion is discussed in U.S. Pat. No. 4,240,925. To prevent conventional pitting corrosion, it has been proposed to employ a so-called anodic inhibitor to prevent the oxidation of iron and a cathodic inhibitor to prevent the corresponding reduction of oxygen to hydroxyl ion. The two half reactions, being inhibited, cannot then form a redox couple to promote rusting corrosion as follows:

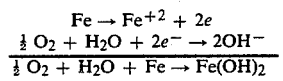

It has been found that the use of organophosphorous insecticides, such as chlorpyrifos, (0, 0-diethyl-0-(3,5,6-trichloro-2-pyridyl) phosphorothioate, presents especially severe pitting corrosion problems to aerosol containers. Such containers are formed of rolled steel which is electrolytically coated with tin-plate and, optionally, with an organic film. Aqueous based, pressurized chlorpyrifos-containing compositions in aerosol cans exhibit shelf lives typically from three months to two years, depending upon the concentration of the pesticide. At lower concentrations of chlorpyrifos on the order of 0.5% by weight the critical shelf life can be on the order of 18 months, but at higher concentrations, the shelf life can be very short.

Recently, it has become highly desirable to provide concentrated chlorpyrifos-containing aerosol compositions. Such compositions are used in specifically adapted aerosol cans which are attached to the end of a garden hose. The concentrated solution is diluted with gardening water and immediately sprayed onto a desired application area in the proper dilution ratio to water.

Aqueous aerosol compositions, typically containing 2 to 5% organophosphorous insecticides have not, until now, been suitable for use in aerosol cans, since severe pitting corrosion occurs usually after only three months of storage. At higher temperatures such pitting corrosion occurs even more rapidly. Conventional corrosion inhibitors such as sodium benzoate, sodium nitrite, butoxyne, sodium citrate, sodium chromate and the like have not proved effective in preventing such pitting corrosion.

A corrosion inhibiting system has been proposed to prevent pitting corrosion in a pressurized rug cleaning composition. That composition, also known as Glory rug cleaner, is an aqueous pressurized solution (not emulsion) of various surfactants which is adapted to be sprayed onto a dirty rug. To stabilize the aerosol can containing the rug cleaning solution against conventional pitting corrosion, an inhibitor system of a (a) terpolymer of styrene-methyl methacrylate-maleic acid; (b) ammonia; (c) sodium benzoate and (d) disodium phosphate has been employed.

The mechanism of pitting corrosion in the pressurized rug cleaning solution is believed to be influenced by the presence of copper. Copper wire, employed in the process for forming the aerosol can, becomes incorporated in the can, itself. The copper and iron undergo a galvanic cell reaction during storage in the aqueous solution, such that the copper tends to plate out on the tin-plate, while the iron is oxidized, thus causing pitting corrosion. It is postulated that the terpolymer acts as a chelating agent for the copper ions to prevent the copper from plating out as copper metal. In the absence of the terpolymer the aerosol cans containing the rug cleaning solution rapidly puncture from pitting corrosion.

It is also believed that the ammonia, which is employed, in part, to stabilize the composition at a high pH, also acts to complex copper ions, thus also preventing copper metal from plating out. It is believed that the sodium benzoate inhibits the oxidation of iron, while the disodium phosphate acts to inhibit the reduction of dissolved oxygen to hydroxyl ion.

It is not possible to use the above-noted rug cleaner inhibitor system in an aqueous, emulsified, pressurized pesticide composition, since the terpolymer of styrene-methylmethacrylate-maleic acid breaks the emulsion. In addition, at the high alkaline pH of 9 typically produced by the ammonia, the emulsion is likewise broken.

Accordingly, it is an object of this invention to provide a pressurized, emulsified organophosphorous formulation having therein an effective corrosion inhibiting system to enable the composition to be stored in aerosol cans.

SUMMARY OF THE INVENTION

It has now been found that the above and other objects are attained in a corrosion-resistant insecticidal composition for use in aerosol containers comprising:
(a) an organophosphorous pesticide;
(b) an organic corrosion inhibitor;
(c) an inorganic corrosion inhibitor;
(d) an emulsifier;
(e) an aerosol propellant; and
(f) an aqueous carrier.

The weight ratio of the organic inhibitor to the inorganic inhibitor in the composition is from about 20:1 to 1:1 and the total weight of the organic inhibitor and the inorganic inhibitor is from about 0.37 to 8% based on the total weight of the composition.

In general, the organic inhibitors are anionic organic compounds while the inorganic inhibitors are preferably Group IA metal salts of inorganic acids.

While the exact mechanism of pitting corrosion in aerosol cans containing a pressurized emulsified organophosphorous pesticide has not been confirmed by the inventors, nonetheless it is postulated that the copper ions and any other transition metal ions present as impurities in the aqueous system, act to catalytically hydrolyze the organophosphorous compounds. Generally, all organophosphorous pesticides are neutral phosphoryl or thiophosphoryl compounds and many of them are ester derivatives. Triesters of phosphoric acid (such as chlorpyrifos) are particularly susceptible to alkaline hydrolysis. The resulting hydrolyzed diester, for example, a phosphorothioic acid, is known to be readily oxidized and to split off a sulfhydryl group.

At a pH (8-13) the sulfhydryl group is reduced, while in another half cell reaction, iron is oxidized. The resulting end product is ferrous sulfide.

In addition, dissolved oxygen in the system is also available to engage in a half cell reaction coupled with the oxidation of iron to provide a more conventional rusting reaction. The overall corrosion reaction may be understood as follows:

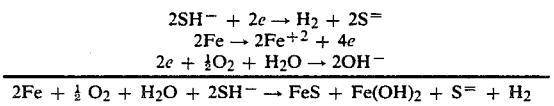

$$2SH^- + 2e \rightarrow H_2 + 2S^=$$
$$2Fe \rightarrow 2Fe^{+2} + 4e$$
$$2e + \tfrac{1}{2}O_2 + H_2O \rightarrow 2OH^-$$
$$\overline{2Fe + \tfrac{1}{2}O_2 + H_2O + 2SH^- \rightarrow FeS + Fe(OH)_2 + S^= + H_2}$$

It is postulated that the organic inhibitor, such as sodium benzoate, acts to complex copper ion to prevent its catalyzing the hydrolysis of the pesticide. It is also possible that the organic inhibitor reacts with the sulfhydryl group to tie up that group and to prevent its reaction with iron. The inorganic corrosion inhibitor is believed act to prevent the cathodic reduction of dissolved oxygen.

In general, sufficient corrosion inhibitors should be present to passivate the aerosol container by forming a film on the interior metal surface to retard corrosion. In addition, it is important to maintain the desired ratio of organic inhibitor to inorganic inhibitor to stabilize the emulsion and also to prevent pitting corrosion.

DETAILED DESCRIPTION OF THE INVENTION

The organophosphorous pesticides employed in the invention are typical neutral phosphoryl or thiophosphoryl compounds having insecticidal activity. Such compounds are employed to control cockroaches, fleas, ants, household pests, turf pests, termites, wood destroying insects, mosquitoes, wood destroying insects, cattle ticks, parasites and the like. Typical organo pesticides useful in the invention include:

| Name | Structure |
|---|---|
| Paraoxon |  |
| Parathion |  |
| Parathion-methyl |  |
| Penitrothion |  |

-continued

| Name | Structure |
|---|---|
| Penthion |  |
| Penchlorphos |  |
| Demeton-S-methyl | $(CH_3O)_2P(O)SC_2H_4SO_2C_2H_5$ |
| Oxydemeton-methyl | $(CH_3O)_2P(O)SC_2H_4SOC_2H_5$ |
| Deoxydemeton-S-methyl | $(CH_3O)_2P(O)SC_2H_4SC_2H_5$ |
| Demeton-S | $(C_2H_5O)_2P(O)SC_2H_4SC_2H_5$ |
| Thiometon | $(CH_3O)_2P(S)SC_2H_4SC_2H_5$ |
| Disulfoton | $(C_2H_5O)_2P(S)SCH_2H_4SC_2H_5$ |
| Phorate | $(C_2H_5O)_2P(S)SCH_2$ |
| Phorate-O-analog | $(C_2H_5O)_2P(O)SCH_2SC_2H_5$ |
| Carbophenothion |  |
| Phenkapton |  |
| Ethion | $(C_2H_5O)_2P(S)SCH_2SP(S)(OC_2H_5)_2$ |
| Azinphosmethyl |  |
| Dimethoate | $(CH_3O)_2P(S)SCH_2CONHCH_3$ |
| Morphothion |  |
| Mecarbam | $(C_2H_5O)_2P(S)SCH_2CON(CH_3)CO_2C_2H_5$ |
| Menazon |  |
| Malathion | $(CH_3O)_2P(O)SCHCO_2C_2H_5$<br>$\quad CH_2CO_2C_2H_5$ |
| Malaoxon | $(CH_3O)_2P(S)SCHCO_2C_2H_5$<br>$\quad CH_2CO_2C_2H_5$ |
| Dichlorvos | $(CH_3O)_2P(O)OCH{=}CCl_2$ |
| Trichlorphon | $(CH_3O)_2P(O)CH(OH){-}CCl_3$ |

-continued

| Name | Structure |
|---|---|
| Chlorfenvinphos | $(C_2H_5O)_2P(O)OC=CHCl$ with 2,4-dichlorophenyl group |
| Mevinphos alpha | $(CH_3O)_2P(O)O-C(CH_3)=C(H)CO_2CH_3$ |
| Mevinphos β | $(CH_3O)_2P(O)OC(CH_3)=C(H)CO_2CH_3$ |
| Phosphamidon alpha | $(CH_3O)_2P(O)OC(CH_3)=C(Cl)-CON(C_2H_5)_2$ |
| Phosphamidon beta | $(CH_3O)_2P(O)OC(CH_3)=C(Cl)CON(C_2H_5)_2$ |
| Diazinon | $(C_2H_5O)_2P(S)O$—pyrimidine with $CH_3$ and $i-C_3H_7$ |
| Thionazin | $(C_2H_5O)_2P(S)O$—pyrazine |
| Thionazin-O-analog | $(C_2H_5O)_2P(O)O$—pyrazine |
| Dimefox | $((CH_3)_2N)_2P(O)F$ |
| Scaradon | $((CH_3)_2N)_2P=O)_2O$ |

A particularly preferred pesticide is chloropyrifos or 0,0-diethyl-0-(3,5,6-trichloro-2-pyridyl) phosphorothioate.

Unless otherwise indicated, the following weights are based on the total weight of the composition of the invention.

In general, the organophosphorous pesticide is employed in amounts from about 0.25 to 5% by weight and, preferably from about 3 to 4% by weight.

The organic chemical inhibitor of the inventor is adapted to prevent catalytic hydrolysis of the organophosphorous pesticide by transition metal ions such as copper, and is adapted to form a passivating film on the tinplate. In general, organic anionic compounds are suitable for those purposes.

Typical organic chemical inhibitors include chelating agents which are non-reactive with the organophosphorous pesticides. Other typical organic chemical inhibitors include heterocyclic compounds such as imidazolene and 2-mercaptobenzothiazole. Di and poly-carboxylic acids, such as oxalic, citric, tartaric and maleic acids, as well as their ammonium and metal salts, especially Group IA metal salts can be employed. Phytic acid is also an effective organic chemical inhibitor.

Other suitable organic corrosion inhibitors include alkyl phosphonates and alkyl phosphate esters. In addition, sodium lauryl sarcosinate and sodium lauryl boroglutonate can be employed.

Best results are obtained, and accordingly, it is preferred that the organic chemical inhibitor is sodium benzoate.

In general, from about 0.25 to 5% by weight of the organic inhibitor is employed and, preferably, from about 0.3 to 2% is utilized in the compositions of the invention.

The inorganic chemical inhibitor of the invention inhibits corrosion, it is postulated, by forming a passivating film over the surface of the iron to prevent oxidation. Typical inorganic chemical inhibitors include, for example, Group IA metal salts of inorganic acids, such as sodium chromate, sodium dichromate, potassium chromate, sodium nitrite, monosodium phosphate, ortho phosphates, sodium molybdate, and sodium hexametaphosphate. Best results are obtained when the inorganic chemical inhibitor is disodium phosphate.

In general, the inorganic inhibitors are employed in amounts sufficient to form a passivating film to block iron oxidation. For this and other purposes from about 0.125 to 2.5% by weight, preferably from about 0.5 to 1% by weight, are employed.

Accordingly, to inhibit pitting corrosion, at least about 0.37% by weight of the total weight of the organic and inorganic corrosion inhibitors, is employed. At that inhibitor level the aerosol can may be subject to some detinning. For best results, to prevent pitting corrosion, general rusting corrosion and detinning, the total amount of inhibitors employed is at least about 0.75% and more preferably at least about 1.5% by weight.

It has been found that it is also important to utilize the proper ratio of organic inhibitor to inorganic inhibitor to prevent destabilization of the emulsion and to inhibit corrosion. For these and other purposes the weight ratio of the organic inhibitor to inorganic inhibitor is from about 20:1 to 1:1, and more, preferably, from about 2:1 to 5:1.

The aqueous aerosol composition is formulated into an oil -in- water emulsion with an appropriate emulsifying or surface active agent, system. The particular emulsifying system employed is not critical to the invention. However, highly anionic surface active agents are not preferred since they are strong electrolytes and may promote corrosion. As employed herein, the term "emulsifier" is intended to include one or more emulsifying agents.

Anionic emulsifiers, which are weak electrolytes can be employed, such as the ammonium and di- and triethanol ammonium salts of long chain fatty acids, alkyl sulfates, alkyl sulfonates, alkaryl sulfates and the like.

If desired, self-emulsifying esters of fatty acids, as glycerol monostearate, can be employed in combination with a low concentration of an anionic agent, such as potassium stearate.

Best results are obtained, when nonionic surface active agents are employed. Such agents generally exhibit low toxicity and are noncorrosive. In general, the preferred nonionic emulsifiers employed in the aerosol composition, include the polyoxyethylene sorbitan esters, the polyoxyethylene fatty ethers, the alkyl phenoxy polyethoxy ethanols, fatty acid esters and the alkanolamides.

The preferred nonionic emulsifiers include ethylene oxide condensates with higher alkylphenols. The preferred ones include ethylene oxide condensates of nonylphenol.

Other preferred nonionic emulsifiers include the polyoxyalkylene esters of organic acids, such as higher fatty acids, rosin acids, tall oil acids and the like. Such esters generally contain from about 10 to 22 carbon atoms in the acid moiety and from about 8 to 30 moles of ethylene oxide or its equivalent in the polyethoxy moiety.

Another preferred class of nonionic emulsifiers are the oxyalkylated higher aliphatic alcohols. Such fatty alcohols preferably contain from about 6 to 11 carbon atoms and are condensed with from 5 to 9 moles of ethylene oxide.

Mixtures of such anionic and nonionic emulsifiers, as well as mixtures of either such anionic emulsifiers or such nonionic emulsifiers are also employed.

In general, the emulsifier is employed in amounts from about 2.5 to 20% by weight, and, more preferably, in amounts from about 4 to 12% by weight.

Especially enhanced results are obtained when a mixture of emulsifiers, including (1) a polyoxyethylene fatty polyol esterified with a fatty acid and (2) a polyoxyethylene ether are employed. In general, in that mixture, each such emulsifier is employed in amounts from about 1.25 to 10% by weight, preferably from about 2 to 6% by weight.

In order to form a stabilized water-out emulsion, it is preferred that the hydrophobic-lipophobic balance (HLB) of the emulsifier system should be from about 10–20.

The propellant employed in the composition of the invention includes the "Freon" propellants and other fluorinated propellants, other liquified gas propellants, such as dimethyl ether and vinyl chloride, compressed gas propellants such as nitrogen, carbon dioxide and nitrous oxide and mixtures of liquified gases and compressed gases.

In order to reduce environmental pollution, it is preferred to employ as the propellant, liquified saturated hydrocarbons comprising one or more liquified saturated hydrocarbons containing 3 or 4 carbon atoms, especially propane, isobutane, normal butane and mixtures thereof.

In general, the propellants are employed in conventional amounts, typically from about 5 to 30% by weight and preferably about 10% by weight.

It has been found that the liquified saturated hydrocarbons may present additional corrosion problems to the composition. Accordingly, it may be desirable to employ a specific inhibitor to meet such problems such as a nitroalkane, especially nitromethane, nitroethane or 2-nitropropane. For this and other purposes, the nitroalkane may be employed in amounts from about 0.01 to 2%, and especially 0.5% by weight.

An aqueous carrier, such as water, is employed to form the stabilized pressurized emulsion. The amount of water employed is not critical and is generally from about 10 to 90%, more preferably from 50 to 80% and, most preferably, from 65 to 75% by weight of the total composition.

Other compatible conventional additives employed in water-based aerosol compositions can also be employed herein.

In general, to prepare the pressurized aerosol composition of the invention, the desired charge of water is introduced into an aerosol can. Thereafter, in sequence, the emulsifier, insecticide, and corrosion inhibitors are introduced into the aqueous composition. The composition is then pressurized with the desired propellant and the final pressurized composition shaken to disperse the ingredients uniformly in the aerosol can.

The following examples illustrate a preferred embodiment of the invention and are not limitative of scope.

EXAMPLE 1

In order to demonstrate the anticorrosion properties of the inventive composition an insecticidal formulation was charged to two tin-plated aerosol containers having linings commercially available as:

(i) Conoweld II, 195 GLD #25, 392 GLD soldered side seam (s.s.s.), sold by Continental Can Co. and (ii) SW IL-30, lined #25, no. s.s.s., sold by Sherwin Williams.

The following composition was charged to each container:

| Composition of Example I | |
|---|---|
| Ingredient | Amount (wt. %) |
| Chlorpyrifos (3.8% actives) | 6.20 |
| *Atplus 540 | 5.00 |
| **Tween 85 | 5.00 |
| Sodium benzoate | 1.00 |
| Disodium phosphate | 0.50 |
| Nitroethane | 0.50 |
| Isobutane | 10.00 |
| Water | 71.80 |
| | 100.00% |

*Atplus 540 is a blend of polyoxyethylene ether (75%); isopropanol (20%) and water (5%))
**Tween 85 is polyoxyethylene (20 moles) sorbitan trioleate The compositions were prepared by charging into the aerosol cans sequentially, the water, emulsifiers, chlorpyrifos, and corrosion inhibitors. The cans were then pressurized with isobutane and shaken. The filling temperature was maintained between about 60°–70° F.

The filled aerosol cans were then subjected to an Accelerated Corrosion Test (ACT) and a Dead Storage Test. The Accelerated Corrosion Test was conducted by impressing a 1500 to 900 millivolt potential for 7 days between the can and a submerged carbon electrode within the can as presented by L. S. Su and E. Sheppard in *CORROSION*, Vol. 31, No. 6, (1975). The can was then opened and inspected for corrosion.

The Dead Storage Tests (Test Packs) were conducted generally in accordance with CSMA-Aerosol Guide Storage Tests, Seventh Edition, April 1981, as approved by Aerosol Division Scientific Committee.

Three control compositions were also tested: Composition A; Composition B and Composition C. Composition A was identical to the inventive composition but did not contain any corrosion inhibitor; Composition B contained 1% sodium benzoate and no disodium phosphate; Composition C contained 1% disodium phosphate and no sodium benzoate. The following results were obtained as set forth in Table 1:

| Formulation | Accelerated Corrosion Test | Dead Storage Test Results |
|---|---|---|
| Example 1 | | |
| (a) Conoweld can | passes; no rust or pitting | 1. after 3.5 months @ R.T. - passes<br>2. after 3.5 months @ 100° F. - possible pitting |
| (b) Sherwin-Williams can | passes | not tested |
| Composition A | | |
| (a) Conoweld can | passes | After 2.5 months @ R.T., pitting observed |
| (c) Sherwin-Williams can | deep pitting and surface rust | not tested |
| Composition B | | |
| (a) Conoweld can | passes | 1. after 3.5 months @ R.T. - passes test<br>2. after 3.5 months @ 100° F., enamel is soft, blistered and pitting observed |
| (b) Sherwin-Williams can | passes | not tested |
| Composition C | | |
| (a) Conoweld can | passes, but rust on valve cap | 1. after 2.5 months @ R.T. - rust in spout<br>2. after 2.5 months @ 100° C. - pitting observed below level of product |
| (b) Sherwin-Williams can | deep pitting | not tested |

EXAMPLE II

Two pressurized aerosol compositions were prepared in accordance with Example I with the exception that the following amounts of inhibitor were employed:

| | |
|---|---|
| Sample 1 | = 0.50 weight % sodium benzoate<br>0.25 weight % disodium phosphate |
| Sample 2 | = 2.0 weight % sodium benzoate<br>1.0 weight % disodium phosphate |

The Samples were subjected to an Accelerated corrosion Test and Sample 1 exhibited substantial detinning, but no pitting, while Sample 2 exhibited no corrosion at all. Sample 2 also showed no corrosion after one year at dead storage.

The invention is not to be limited except as set forth in the following claims:

Wherefore, we claim:

1. An aqueous-based corrosion resistant insecticidal composition for use in aerosol containers subject to pitting corrosion comprising:
   (a) an organophosphorous pesticide selected from the group consisting of neutral phosphoryl compounds and thiophosphoryl compounds, said organophosphorous pesticide present in amounts of from about 3.0 to 4.0% by weight;
   (b) sodium benzoate present in amounts from about 0.3 to 2% by weight;
   (c) disodium phosphate present in amounts from about 0.15 to 1% by weight;
   (d) a nonionic emulsifier present in amounts from about 4 to 12% by weight;
   (e) a liquified saturated hydrocarbon selected from the group consisting of propane, isobutane, normal butane and mixtures thereof; and
   (f) water,
wherein the weight ratio of the sodium benzoate to disodium phosphate is from about 3:1 to 2:1 and the combined weight of said sodium benzoate and said disodium phosphate is at least about 0.75% of the total weight of the insecticidal composition.

2. In an insecticidal composition for use in aerosol containers subject to pitting corrosion comprising an organophosphorous pesticide in an amount of about 2 to about 5% by weight, an emulsifier in an amount of from about 2.5 to 20% by weight, an aerosol propellant and an aqueous carrier, the improvement which comprises:
   (a) an organic corrosion inhibitor to prevent hydrolysis of the organophosphorous pesticide, wherein said corrosion inhibitor is sodium benzoate employed in amounts of from about 0.25 to about 5.0% by weight; and
   (b) an inorganic corrosion inhibitor in an amount of about 0.125 to about 2.5% by weight, wherein said inorganic corrosion inhibitor is disodium phosphate;
wherein the weight ratio of said organic inhibitor to said inorganic inhibitor is from about 20:1 to about 1:1 and the total weight of said organic inhibitor and said inorganic inhibitor is from about 0.37 to about 8.0% based on the total weight of the composition.

* * * * *